United States Patent [19]
Berg

[11] Patent Number: 5,231,285
[45] Date of Patent: Jul. 27, 1993

[54] REFRACTION INDEX CHANGE MEASUREMENT

[75] Inventor: Ralph T. Berg, Ramsey, Minn.

[73] Assignee: Honeywell Inc., Minneapolis, Minn.

[21] Appl. No.: 979,364

[22] Filed: Nov. 20, 1992

Related U.S. Application Data

[63] Continuation of Ser. No. 723,353, Jun. 28, 1991, abandoned.

[51] Int. Cl.$^5$ .................... G01D 5/34; G01B 11/02
[52] U.S. Cl. .................... 250/231.1; 356/357; 356/128
[58] Field of Search .............. 356/361, 356, 357, 358, 356/128, 133; 250/231.1, 573, 231.11, 429, 238, 370.15, 443.1; 73/863.11

[56] References Cited

U.S. PATENT DOCUMENTS

| | | | |
|---|---|---|---|
| 3,930,730 | 1/1976 | Laurens et al. | 356/357 |
| 3,950,104 | 4/1976 | Munk | 356/128 |
| 4,425,810 | 1/1984 | Simon et al. | 73/863.11 |
| 4,989,980 | 2/1991 | Berg | 356/356 |
| 5,121,987 | 6/1992 | Berg | 356/357 |

Primary Examiner—Davis L. Willis
Assistant Examiner—Hoa Q. Pham
Attorney, Agent, or Firm—Robert A. Pajak

[57] ABSTRACT

A method and apparatus for measuring the change in refractive index of a material with respect to temperature. The invention contemplates measuring the change in length of the material with respect to temperature over a predetermined temperature range with a Fizeau Interferometer by measuring the change in length through a vacuum at a point adjacent the length to produce a first set of data. Also measured is the change in the same length of the same material with respect to temperature over the same predetermined temperature range with the Interferometer by measuring the change in the length through the material to produce a second set of data. Determining the difference between the first and second sets of data produces resulting data which is the change in refractive index of the material with respect to temperature.

11 Claims, 2 Drawing Sheets

REFRACTION INDEX CHANGE MEASUREMENT

This application is a continuation, of application Ser. No. 07/723,353, filed Jun. 28, 1991, now abandoned.

FIELD OF THE INVENTION

The present invention relates to a method and apparatus for measuring the change of the refractive index of a material with respect to change in temperature. More particularly, the present invention relates to a method using a spectrometer to directly measure the change in refractive index with respect to change in temperature with increased sensitivity and superior thermal control.

BACKGROUND OF THE INVENTION

The field of optics has had a long and unfilled need for a cost efficient and accurate system for measuring various properties of materials such as quartz, glass, and the like. One system has recently been discovered in which the coefficient of thermal expansion the (CTE) of optical glass may be measured accurately using apparatus and a method disclosed in my commonly owned application for A METHOD AND APPARATUS FOR MEASURING COEFFICIENT OF THERMAL EXPANSION, now U.S. Pat. No. 4,989,980.

The method disclosed in my patent includes the steps of generating an interference pattern defined by Newton rings which are a function of the specific material being examined. The area of at least one Newton ring is measured, and then the magnitude of change is the dimension is determined as a function of changes in area of that Newton ring. When temperature is used to change the dimension, a coefficient of thermal expansion can be calculated. A scale factor is determined which is a function of the difference between the area of a pair of successive Newton rings and of the wavelength of the laser beam.

The measurement of the area of the Newton rings is most difficult to measure precisely. These rings are not perfect circles with easy to measure areas. To more effectively use the apparatus in my patent, a method for calculating the area of an image, such as Newton rings which are produced by laser beam interference on a test sample was developed and is the subject of co-pending U.S. patent application for READOUT SYSTEM FOR DILATOMETERS, having Ser. No. 706,686, filed May 29, 1991 in the name of Hansen and commonly owned. The method includes a plurality of steps which permit computer operation to automate the procedure. Video images of Newton rings or fringes are taken, such as at various temperatures or under other conditions which might be varied to observe the changes in the test sample caused by the varied conditions. The area of the fringe or fringes is determined using a computer implemented algorithm.

Those new methods and apparatus described in the aforementioned patent and application are designed generally to measure test sample dimensional changes as a function of temperature so as to determine the coefficient of thermal expansion of optical materials. It would be of great advantage to the art if there would be a way to measure other important material properties beyond that of CTE.

One important property which is not presently measured directly in the optical field is the change in refractive index of a material with respect to the change in temperature of the material. Present methods measure indirect changes, by measuring changes in a bending angle with temperature. The prior art does not contain a method of measuring direct changes in the optical path length with respect to temperature. The prior art methods include measurements of angles with respect to temperature and have relatively low sensitivity. Thermal control is poor and therefore the method is much less accurate.

For that reason, it is an object of this invention to provide a method for directly measuring changes in refractive index of materials with respect to changes in temperature.

Another object is to employ new devices which have been developed for optical measurements and evaluation, such as my patent and the application described above, and to use these new methods to produce additional information such as change in refractive index with respect to temperature.

Other objects will appear hereinafter.

SUMMARY OF THE INVENTION

It has now been discovered that the above and other objects of the present invention may be accomplished in the following manner. Specifically a new method and apparatus for measuring the change in refractive index of a material of a selected test sample with respect to temperature has been discovered.

The invention includes a method and apparatus for measuring the change in length of a test sample with respect to temperature over a predetermined temperature range, preferably with a Fizeau Interferometer by measuring the change in an optical path length through a vacuum adjacent a length-wise dimension of the test sample to produce a first set of data. Also measured is the change in the same length of the same test sample with respect to temperature over the same predetermined temperature range with the Interferometer by measuring the change in the optical length through the material adjacent the same length-wise dimension of the test sample to produce a second set of data.

When "l" represents the length of the material and "n" represents the refractive index, the change in refractive index with respect to temperature is derived from the two sets of data as follows. The first set of data produces a set representing dl/l versus temperature. The second set of data produces a set representing dl/l and dn/l versus temperature. Determining the difference between the first plus second sets of data produces resulting data dn/dT, which is the change in refractive index n of the material with respect to temperature.

Preferably the test sample of the material is in the shape of a hollow, right cylinder, and the length is measured axially in parallel with the outer wall portion of the cylinder. The first set of data is produced by passing an optical beam of light, as part of the Fizeau Interferometer, through the hollow central portion and substantially in parallel with the central axis of the cylinder, and the second set is produced by passing the optical beam of light through the material of the test sample in parallel with the central axis of the cylinder. While any temperature range can be used, valuable data is often desired over the range of temperature from about $-100°$ F. to about $+200°$ F.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
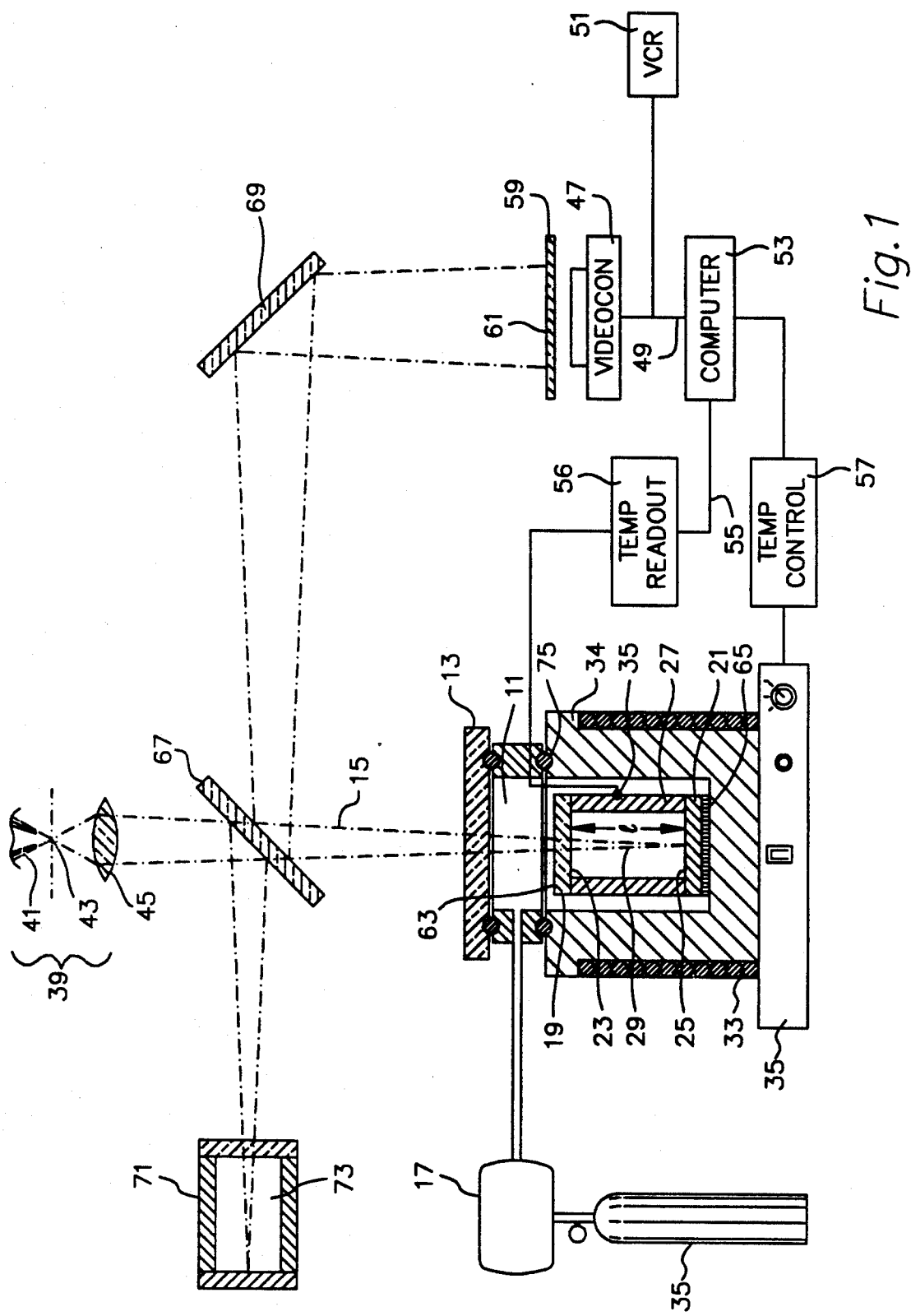
FIG. 1 illustrates a schematic view of a Fizeau Interferometer system which is part of the preferred embodiment of the present invention, shown arranged for measurement and collection of a first set of data.
Figure 2:
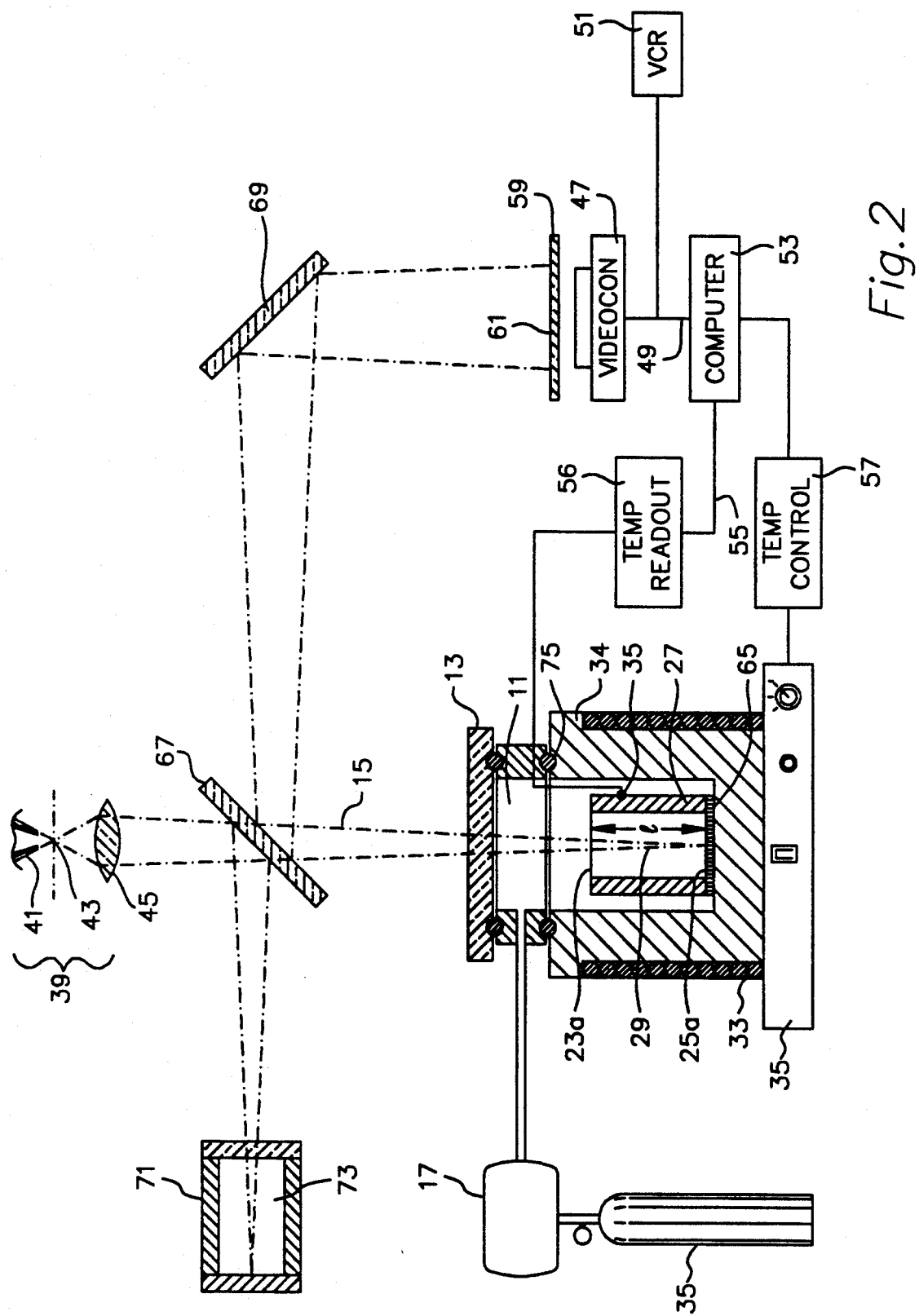
FIG. 2 illustrates a schematic view of a Fizeau Interferometer system which is part of the preferred embodiment of the present invention, shown arranged for measurement and collection of a second set of data.

In FIG. 1 and FIG. 2, a schematic view of the present invention is shown in use with a Fizeau Interferometer of the type described in U.S. Pat. No. 4,989,980, coupled to a dilatometer readout system of the type described in the above identified commonly owned Hansen U.S. patent application for READOUT SYSTEM FOR DILATOMETERS, having Ser. No. 706,686, filed May 29, 1991. It is intended that the present invention be understood as being useful with this particular system, although it is also useful with other equipment which would be capable of measuring change in length versus temperature.

Shown in FIG. 1 is an optical dilatometer system 10 which employs a Fizeau interferometer in combination with a focused laser beam 15 to generate an interference pattern 61. The system 10 includes an interferometer having a chamber 11 which includes transparent end 13 for receiving beam 15 into chamber 11. O ring seals 75 provide an airtight seal so that pump 17 can maintain a vacuum within chamber 11.

The temperature within chamber 11 may be varied by many means. Shown in FIG. 1 is a heat source 35 used with liquid nitrogen coils 33 acting on a substantial mass 34. Mass 34 is, for example, a 30 pound mass of copper which functions as a heat reservoir.

System 10 also includes a helium source 37 in order to introduce helium into chamber 11 between uses of the system in order to enhance thermo-conductivity within the chamber 11 and thereby expedite a temperature change in preparation for taking measurements. Of course, once the desired temperature is reached, the helium is then pumped out of the chamber 11, returning to a vacuum state for operation of the system.

A test sample 27 is enclosed in a chamber structure between first and second interference surfaces 23 and 25, which are surfaces of first and second plates 19 and 21 and which define an axial length l. Sample 27 is made from the material of interest and is preferably formed into a right, hollow cylinder as shown in FIG. 1. The cylindrical sample 27 is centered about the axis of the chamber 11, and beam 15 travels on optical path 29 through a vacuum over length l adjacent to sample 27. As the temperature is varied over a predetermined range of temperature where dl/l is the normalized length change corresponding to a selected change in temperature, data is taken showing the change in length dl/l versus temperature.

All of the interferomic sensing is performed on the test sample 27 within chamber 11, and all of the readout is performed outside chamber 11 and at room temperature, Temperature of the sample 27 is measured via temperature readout 56 and data is sent via line 55 to the computer 53. Also, the ring pattern 61 is viewed on viewing screen 59 to provide the pattern on which the present invention is practiced. This ring pattern 61 is produced on screen 59 and is converted by video camera 47 into digital data, and transmitted via line 49 to VCR 51 and computer 53.

Pattern 61 is transmitted to viewing screen 59 by directing the interference pattern from beam splitter 67 and folding mirror 69. Stabilizing monitor 71 is shown as a means for monitoring the stability of the laser. This is to ensure that the laser emits a constant wavelength and to ensure dimensional stability of the laser. Monitor 71 includes chamber 73 similar to chamber 11.

The system shown in FIG. 2 is functionally similar to the system of FIG. 1, but shows the cylindrical test sample 27 moved in the direction into the plane of the drawing. First and second plates 19 and 21 have been removed so that first and second interference surfaces have become the top 23a and bottom 25a of cylindrical test sample 27. Thus, beam 15 travels through sample 27 as it travels on path 29 as described above. Again, as the temperature is varied over a predetermined range, data is taken. This second set of data shows the sum of the change in length dl/l and the change in refractive index dn/l, where n is the refractive index of the optical material from which sample 27 is made.

It is clear from the above that the laser beam 15 has traveled the same path 29 through a vacuum adjacent sample 27 over length l and through sample 27 itself over the same length l in axially aligned paths. Since the only difference between the two paths is the optical refraction of sample 27, the difference between sets of data from FIG. 1 and FIG. 2 is the change in refractive index of the material with respect to temperature, or dn/dt.

The readout system converts length of sample changes into Newton rings, from which the data is collected using the techniques of the apparatus shown in the incorporated patent and application. It should be noted that the images may be stored electronically using a wide variety of techniques. For example, charge-coupled device arrays and signal process the "visual" image so that it is analyzed by only electronic processing.

The method and apparatus of the present invention have been employed on a wide variety of optical materials, such as glass, quartz and plastics of various compositions. All that is necessary is that the material optically transmit a laser beam so that dl/l can be measured outside the material in a vacuum, and that dl/l +dn/l can be measured by passing the optical beam through the material as described. It is then easy to determine the differences between the two sets of data by simple subtraction. This direct measurement of dn/dT where dT is the change in temperature is produced from the same length of the same material using the same laser and attendant equipment. It is directly measured for the first time, and has been found to be very reproducible and high accurate.

While particular embodiments of the present invention have been illustrated and described, it is not intended to limit the invention, except as defined by the following claims.

I claim:

1. A method of measuring the change in refractive index of a material as a function of temperature, said method comprising the steps of:

determining a first change in length of a selected length-wise dimension of a test sample of a selected material in response to a selected temperature change, said first change in length determined as a function of a first optical path followed by an optical beam passing through a vacuum, substantially in parallel with said length-wise dimension, and wherein said first optical path is affected by said length-wise dimension of said test sample;

determining a second change in length of said selected length-wise dimension of said test sample in response to said selected temperature change as a function of a second optical path followed by an optical beam passing through said test sample materials, substantially in parallel with said length-wise dimension of said test sample; and determining the change in said index of refraction for said selected temperature change as a function of the difference between said first change in length and said second change in length.

2. The method of claim 1 wherein said test sample is in the shape of right circular cylinder having a cylindrical wall portion and said length-wise dimension is the axial length of said cylindrical wall portion.

3. The method of claim 2 wherein said cylinder is hollow, and said first change in length is a function of said first optical path followed by said optical beam passing through said hollow portion of said cylinder, and said second change in length is a function of said second optical path followed by said optical beam passing axially through said cylindrical wall portion.

4. The method of claim 1 wherein said first change in length and said second change in length are obtained by use of a Fizeau interferometer cavity under vacuum, and in which said first and second length changes are between top and bottom surfaces of said cylinder defining said length-wise dimension of said test sample.

5. A method of measuring the change in refractive index of a material with respect to temperature, comprising the steps of:

determining a first change in length of a selected length-wise dimension of a test sample of a selected material with respect to temperature over a pre-determined temperature range with a Fizeau interferometer by measuring said change in length as a function of a first optical path followed by an optical beam passing through a vacuum, substantially in parallel with said length-wise dimension, and wherein said first optical path is affected by said length-wise dimension of said test sample in order to produce a first set of data;

determining a second change in length of said length-wise dimension of said test sample in response to said pre-determined temperature range with said Fizeau interferometer by measuring said second change in length as a function of a second optical path followed by an optical beam passing through said test sample material, substantially in parallel with said length-wise dimensions, and wherein said second optical path is affected by said length-wise dimensions of said test sample in order to produce a second set of data; and determining a change in said index of refraction for said selected temperature range as a function of the difference between said first change in length and said second change in length.

6. The method of claim 5 wherein said test sample is in the shape of a right circular cylinder having a cylindrical wall portion, and said length-wise dimension is the axial length of said cylindrical wall portion, and said cylinder being hollow.

7. The method of claim 5 wherein said first set of data is produced from measurements taken with said optical beam passing axially through said hollow portion of said cylinder, and said second set of data being produced from measurements of said optical beam passing axially through said cylindrical wall portion.

8. The method of claim 5 wherein length of said length-wise dimension is determined by the length between a pair of plates defining top and bottom surfaces of said right circular cylinder, and second change in path length is determined without said plates and defined by top and bottom surfaces of said right circular cylindrical wall portion.

9. A method of measuring the change in refractive index of a material as a function of temperature comprising the steps of:

determining a first change in length of a selected length-wise dimension of a test sample of a selected material in response to a selected temperature change by employing the use of a Fizeau interferometer in which Newton interference rings are established, at least in part, as a function of an optical beam propagating along an optical path, through a vacuum, and between first and second plates which define said length-wise dimension of said test sample;

determining a second change in length of said selected length-wise dimension of said test sample in response to said selected temperature change by employing the use of said Fizeau interferometer in which Newton interference rings are established, at least in part, as a function of an optical beam propagating along an optical path through said test sample material, between first and second end surfaces of said test sample which define said length-wise dimension of said test sample, and substantially in parallel with said length-wise dimensions and determining the change in said index of refraction for said temperature change as a function of the difference between said first change in length and said second change in length.

10. The method of claim 9 wherein said test sample is a right circular cylinder.

11. The method of claim 10 wherein said right circular cylinder is hollow and includes a wall portion in parallel with the cylindrical axis of said cylinder, and in which said first length change is measured with said optical beam passing through said hollow portion of said cylinder, and said second path length change is determined as a function of the optical beam passing through said wall portion of said cylinder.

* * * * *

UNITED STATES PATENT AND TRADEMARK OFFICE
CERTIFICATE OF CORRECTION

PATENT NO. : 5,231,285
DATED : Jul. 27, 1993
INVENTOR(S) : Ralph T. Berg

It is certified that error appears in the above-identified patent and that said Letters Patent is hereby corrected as shown below:

Column 5, line 8, cancel the hyphenated word "materials" and substitute --material--;

line 10, add --, and wherein said second optical path is affected by said length-wise dimension-- after the word "dimension" and before the word "of";

line 54, cancel "dimensions" and substitute --dimension--;

line 56, cancel "dimensions" and substitute --dimension--.

Column 6, line 44, cancel "dimensions" and substitute --dimension;--.

Signed and Sealed this

Fifteenth Day of March, 1994

Attest:

BRUCE LEHMAN

Attesting Officer    Commissioner of Patents and Trademarks